United States Patent
Lee et al.

(10) Patent No.: US 7,859,029 B2
(45) Date of Patent: Dec. 28, 2010

(54) FET-BASED SENSOR FOR DETECTING IONIC MATERIAL, IONIC MATERIAL DETECTING DEVICE USING THE FET-BASED SENSOR, AND METHOD OF DETECTING IONIC MATERIAL USING THE FET-BASED SENSOR

(75) Inventors: Kyu-sang Lee, Yongin-si (KR); Kyu-tae Yoo, Yongin-si (KR); Jeo-young Shim, Yongin-si (KR); Jin-tae Kim, Yongin-si (KR); Yeon-ja Cho, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 823 days.

(21) Appl. No.: 11/621,191

(22) Filed: Jan. 9, 2007

(65) Prior Publication Data
US 2007/0159216 A1    Jul. 12, 2007

(30) Foreign Application Priority Data
Jan. 9, 2006  (KR) ............... 10-2006-0002373

(51) Int. Cl.
  *H01L 29/78* (2006.01)
(52) U.S. Cl. .............. 257/253; 257/E29.242; 257/414; 204/416; 72/23
(58) Field of Classification Search ........... 257/253
  See application file for complete search history.

(56) References Cited

U.S. PATENT DOCUMENTS

| | | | |
|---|---|---|---|
| 4,238,757 A | 12/1980 | Schenck | |
| 4,874,499 A * | 10/1989 | Smith et al. | 204/403.03 |
| 6,085,576 A * | 7/2000 | Sunshine et al. | 73/29.01 |
| 2004/0136866 A1* | 7/2004 | Pontis et al. | 422/57 |
| 2006/0272942 A1* | 12/2006 | Sirringhaus | 204/406 |

FOREIGN PATENT DOCUMENTS

| | | |
|---|---|---|
| EP | 1542009 A1 | 6/2005 |
| EP | 1850124 A2 | 10/2007 |
| JP | 2003322633 | 11/2003 |
| WO | 9947905 | 9/1999 |
| WO | 2005022142 A1 | 3/2005 |
| WO | 2005047878 A1 | 5/2005 |

OTHER PUBLICATIONS

European Search Report; Feb. 28, 2008; 06124405.9-2004.
All references cited in the Search Report and not previously submitted are listed above.

* cited by examiner

Primary Examiner—Jerome Jackson, Jr.
(74) *Attorney, Agent, or Firm*—Cantor Colburn LLP

(57) ABSTRACT

Provided are a FET-based sensor for detecting an ionic material, an ionic material detecting device including the FET-based sensor, and a method of detecting an ionic material using the FET-based sensor. The FET-based sensor includes: a sensing chamber including a reference electrode and a plurality of sensing FETs; and a reference chamber including a reference electrode and a plurality of reference FETs. The method includes: flowing a first solution into and out of the sensing chamber and the reference chamber of the FET-based sensor; flowing a second solution expected to contain an ionic material into and out of the sensing chamber while continuously flowing the first solution into and out of the reference chamber; measuring a current in a channel region between the source and drain of each of the sensing and reference FETs; and correcting the current of the sensing FETs.

12 Claims, 7 Drawing Sheets

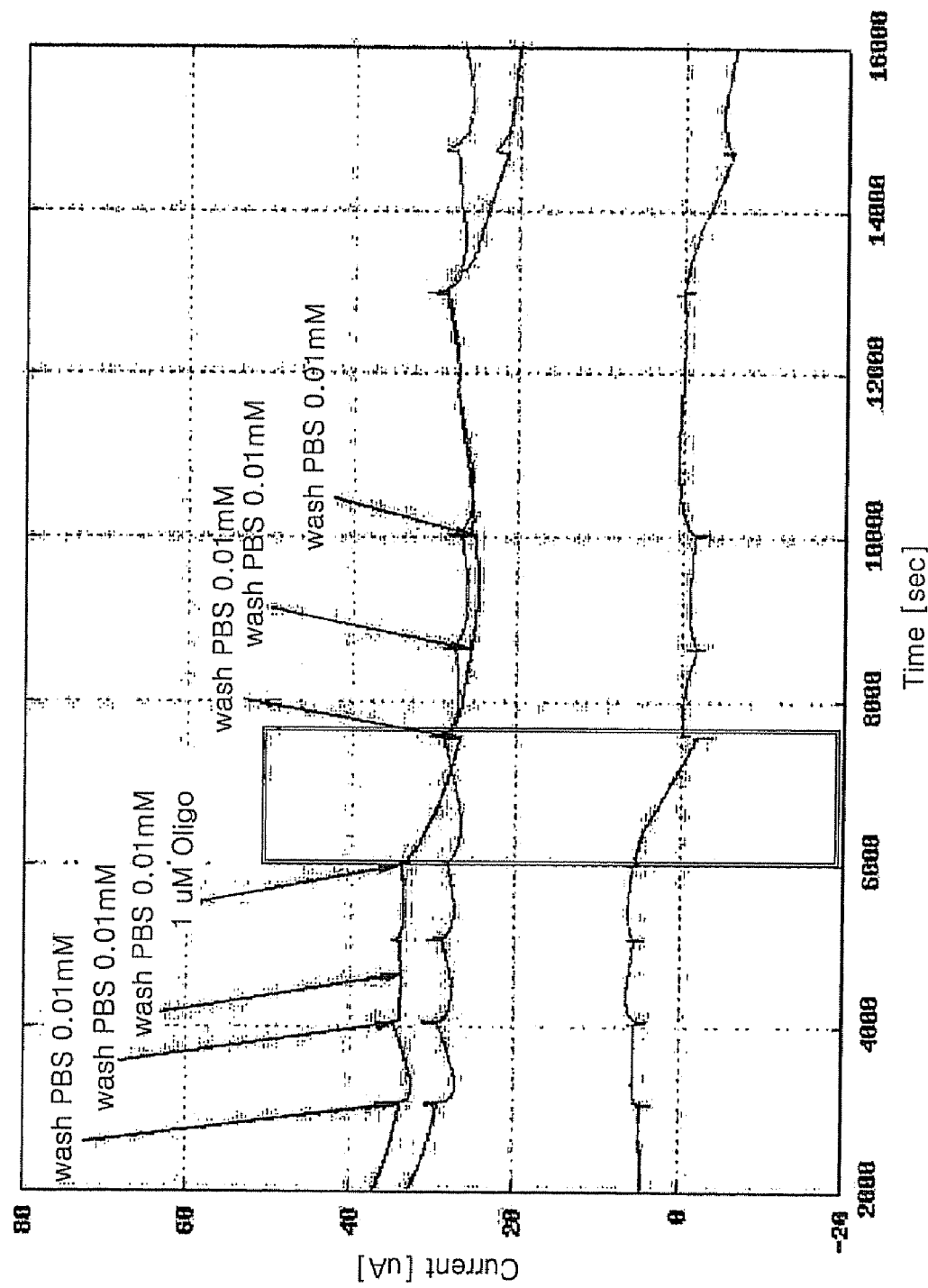

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: oligonucleotide

<400> SEQUENCE: 1
tgttctcttg tcttg                                                    15

FET-BASED SENSOR FOR DETECTING IONIC MATERIAL, IONIC MATERIAL DETECTING DEVICE USING THE FET-BASED SENSOR, AND METHOD OF DETECTING IONIC MATERIAL USING THE FET-BASED SENSOR

This application claims priority to Korean Patent Application No. 10-2006-0002373, filed on Jan. 9, 2006, and all the benefits accruing therefrom under 35 U.S.C. §119, the contents of which in its entirety are herein incorporated by reference.

BACKGROUND OF THE INVENTION

1. Field of the Invention

The present invention relates to a FET-based sensor for detecting an ionic material, a device for detecting an ionic material including the FET-based sensor and a method of detecting an ionic material using the device.

2. Description of the Related Art

Transistor-based biosensors are a kind of sensors detecting ionic materials, especially biomolecules, using electrical signals in aqueous solution. Transistor-based biosensors are manufactured through semiconductor manufacturing processes and have been significantly researched due to the advantages of high-speed signal transition and easy combination with an integrated circuit ("IC") and micro-electro mechanical systems ("MEMS").

U.S. Pat. No. 4,238,757 is a patent relating to the detection of a biological reaction using a field effect transistor ("FET"). This patent relates to a biosensor detecting an antigen-antibody reaction by measuring a current resulting from a change in surface charge concentration in a semiconductor inversion layer. The patent relates to the detection of a protein among biomolecules.

FET biosensors are cost and time efficient compared to conventional methods. In addition, FETs can be relatively easily integrated with IC and MEMS processes.

Probe biomolecules may or may not be fixed to a surface of a gate electrode of the FET-based biosensor. A method of detecting biomolecules using a FET-based biosensor includes measuring a change in current according to the binding of a target biomolecule to a surface of the gate electrode to which probe biomolecules may or may not be fixed. In an alternative method, a change in current according to the presence of a target biomolecule in a certain distance from a gate electrode to which no probe biomolecules are fixed can be measured.

An example of a conventional FET-based biosensor is a sensor including a single FET. Conventional FET-based biosensors, however, cannot separate signals derived from target biomolecules from noise, such as a drift signals spontaneously generated due to a reaction on a surface of a gate electrode, and signals generated due to the pressure of inflowing solution.

Japanese Patent Laid-open No. 2003-322633 discloses another example of a conventional FET-based biosensor including two FETs having different structures and electrical characteristics in a single chamber, wherein probe biomolecules are fixed to a surface of a gate of one of the FETs and the other FET is used as a reference FET.

However, since the two FETs of the biosensor use different surface materials, signals from the reference FET do not show drifting, which occurs in the sensing FET, and thus cannot be used for signal correction. Thus, the sensitivity of the biosensor is still low.

BRIEF SUMMARY OF THE INVENTION

An exemplary embodiment provides a field effect transistor ("FET")-based sensor that can detect a low concentration of ionic materials with high sensitivity.

An exemplary embodiment provides an ionic material detecting device that can detect a low concentration of ionic materials with high sensitivity.

An exemplary embodiment provides a method of detecting an ionic material that can detect a low concentration of ionic materials with high sensitivity.

In an exemplary embodiment there is provided a FET-based sensor for detecting an ionic material. The sensor includes a sensing chamber including a reference electrode and a plurality of sensing FETs and a reference chamber including a reference electrode and a plurality of reference FETs.

In an exemplary embodiment, the sensing FETs and the reference FETs may have a same structure and same electrical characteristics.

In an exemplary embodiment, the sensing FETs and the reference FETs may be arranged in an array form.

In an exemplary embodiment, each of the sensing and reference FETs may include a substrate, a source and a drain that are formed in side regions of the substrate and are doped with a polarity opposite to the substrate and a gate that is formed on the substrate to connect the source and the drain.

In an exemplary embodiment, the gate may include an oxide layer and a polysilicon layer on the oxidation layer.

In an exemplary embodiment, the ionic material may be a biomolecule.

In an exemplary embodiment, the biomolecule may be a nucleic acid or a protein. The nucleic acid may be selected from the group consisting of DNA, RNA, PNA, LNA, and a hybrid thereof. The protein may be selected from the group consisting of an enzyme, a substrate, an antigen, an antibody, a ligand, an aptamer, and a receptor.

In an exemplary embodiment, each of the sensing chamber and the reference chamber may further include an inlet through which a solution flows into the chamber and an outlet through which a solution flows out of the chamber.

In an exemplary embodiment, each of the sensing chamber and the reference chamber may further include a micropump pumping a solution into and out of the chambers.

In an exemplary embodiment, there is provided an ionic material detecting device including the above-described FET-based sensor.

In an exemplary embodiment, there is provided a method of detecting an ionic material using a FET-based sensor. The method includes flowing a first solution into and out of the sensing chamber and the reference chamber of the FET-based sensor, flowing a second solution to be evaluated for an ionic material into and out of the sensing chamber while continuously flowing the first solution into and out of the reference chamber, measuring a current in a channel region between the source and drain of each of sensing and reference FETs while flowing the first and second solutions through the sensing chamber and the reference chamber, respectively, and correcting the current of the sensing FETs by subtracting the current of the reference FET from the current of the sensing FETs. The FET-based sensor includes a sensing chamber including a reference electrode and a plurality of sensing FETs and a reference chamber including a reference electrode and a plurality of reference FETs.

In an exemplary embodiment, the flowing of the second solution into and out of the sensing chamber and the flowing of the first solution into and out of the reference chamber may be performed under a same pressure.

In an exemplary embodiment, the correcting of the current of the sensing FET may include subtracting an average current of the plurality of reference FETs from an average current of the plurality of sensing FETs.

In an exemplary embodiment, the ionic material may be a biomolecule. The biomolecule may be a nucleic acid or a protein. The nucleic acid may be selected from the group consisting of DNA, RNA, PNA, LNA, and a hybrid thereof. The protein may be selected from the group consisting of an enzyme, a substrate, an antigen, an antibody, a ligand, an aptamer, and a receptor.

BRIEF DESCRIPTION OF THE DRAWINGS

The above and other features and advantages of the present invention will become more apparent by describing in detail exemplary embodiments thereof with reference to the attached drawings in which:

FIG. 5B is a graph illustrating the averages of the results in FIG. 5A.

DETAILED DESCRIPTION OF THE INVENTION

Figure 1:
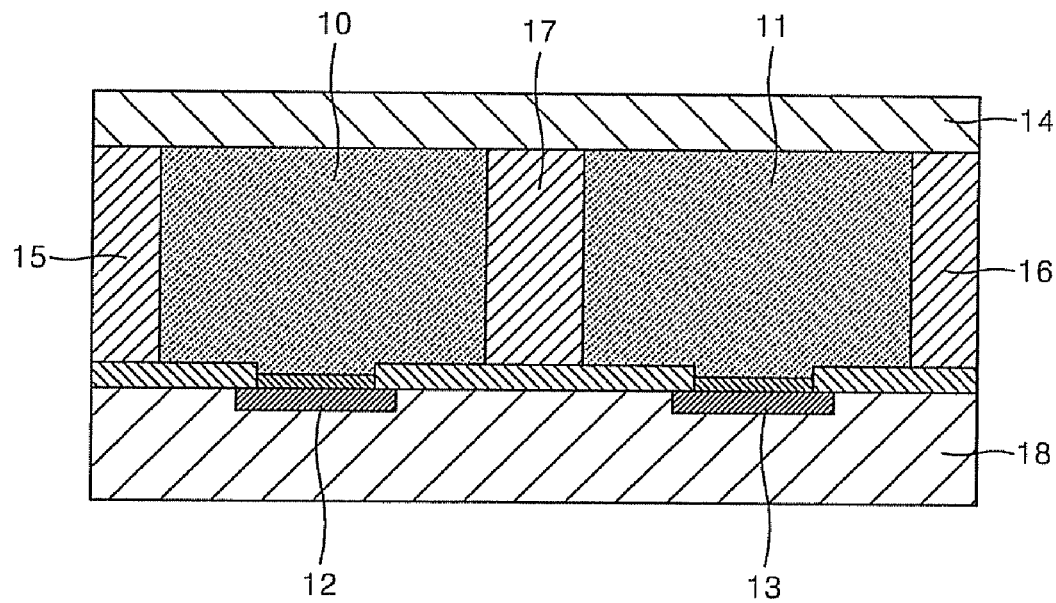
FIG. 1 is a schematic illustration of an exemplary embodiment of a FET-based sensor for detecting an ionic material according to the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention will be described in details with reference to the appended drawings.

The present invention provides a field effect transistor ("FET")-based sensor that can detect a low concentration of ionic materials due to high sensitivity.

FIG. 1 is a schematic illustration of an exemplary embodiment of a FET-based sensor for detecting an ionic material according to the present invention.

Referring to FIG. 1, the FET-based sensor includes a sensing chamber 10 including a reference electrode 14 and a plurality of sensing FETs 12, a reference chamber 11 including the reference electrode 14 and a plurality of reference FETs 13.

Referring to FIG. 1, the sensing chamber 10 is defined by a lower substrate 18, sidewalls 15 and 17, and an upper substrate functioning as the reference electrode 14. The reference chamber 11 is defined by the lower substrate 18, sidewalls 16 and 17, and the upper substrate functioning as the reference electrode 14.

In an exemplary embodiment of a FET-based sensor for detecting an ionic material, the sensing FET and the reference FET can have substantially a same structure and same electrical characteristics. When the sensing FETs and reference FETs are the same structure and the same electrical characteristics, more accurate signals can be detected by correcting signals obtained from the FETs.

In FIG. 1, only one sensing FET 12 and one reference FET 13 are illustrated for the convenience of illustration, but the invention is not limited thereto.

The sensing FETs 12 and the reference FETs 13 may be arranged in various forms in the sensing chamber 10 and the reference chamber 11, respectively. In one exemplary embodiment, the sensing FETs 12 and the reference FETs 13 may be arranged in substantially an array on the same substrate.

In an exemplary embodiment of a FET-based sensor for detecting an ionic material, each FET may include a substrate (not shown), a source (not shown) and a drain (not shown) that are formed in side regions of the substrate and doped to have a polarity opposite to the substrate. A gate (not shown) may be formed on the substrate to connect the source and the drain.

Any of a number of FETs may be used such as those used in a complementary metal-oxide semi-conductor ("CMOS") device. FETs may include, but are not limited to, an n-channel metal-oxide semi-conductor field-effect transistor ("n-MOS") and a p-channel metal-oxide semi-conductor field-effect transistor ("p-MOS"). In one exemplary embodiment, when the substrate is doped with an n-type dopant, the source and the drain can be doped with a p-type dopant. Alternatively, when the substrate is doped with a p-type dopant, the source and the drain can be doped with an n-type dopant.

In a FET, the source supplies carriers, such as free electrons or holes, to the drain, and the gate controls the flow of carriers between the source and the drain. A FET can detect an ionic material without labeling and may be considered one of the most preferred sensor for detecting an ionic material, such as biomolecules, in an electrolyte.

In an exemplary embodiment, the gate may include an oxide layer and a polysilicon layer formed on the oxide layer. A gate with an exposed polysilicon layer can be obtained by removing a passivation layer and a gate electrode layer from a commercially available FET.

Alternatively, the gate may include an oxide layer, a polysilicon layer formed on the oxide layer and a gate electrode layer formed on the polysilicon layer. The gate electrode layer may be formed of any of a number of materials, such as gold.

In exemplary embodiments, the ionic material is not specifically limited to a certain kind. In one exemplary embodiment, the ionic material can be biomolecules, such as a nucleic acid or protein.

The nucleic acid may be selected from the group consisting of a deoxyribonucleic acid (DNA), a ribonucleic acid (RNA), a peptide nucleic acid (PNA), a locked nucleic acid (LNA), and a hybrid thereof. The protein can be selected from the group consisting of an enzyme, a substrate, an antigen, an antibody, a ligand, an aptamer and a receptor.

In an exemplary embodiment, each of the sensing chamber and the reference chamber may further include an inlet through which a solution flows in and an outlet through which a solution flows out.

In an embodiment of the present invention, each of the sensing chamber and the reference chamber may further include a micropump pumping a solution in to and out of the chambers.

An illustrated exemplary embodiment also provides an ionic material detecting apparatus that can detect a low concentration of ionic materials with high sensitivity.

Figure 2:
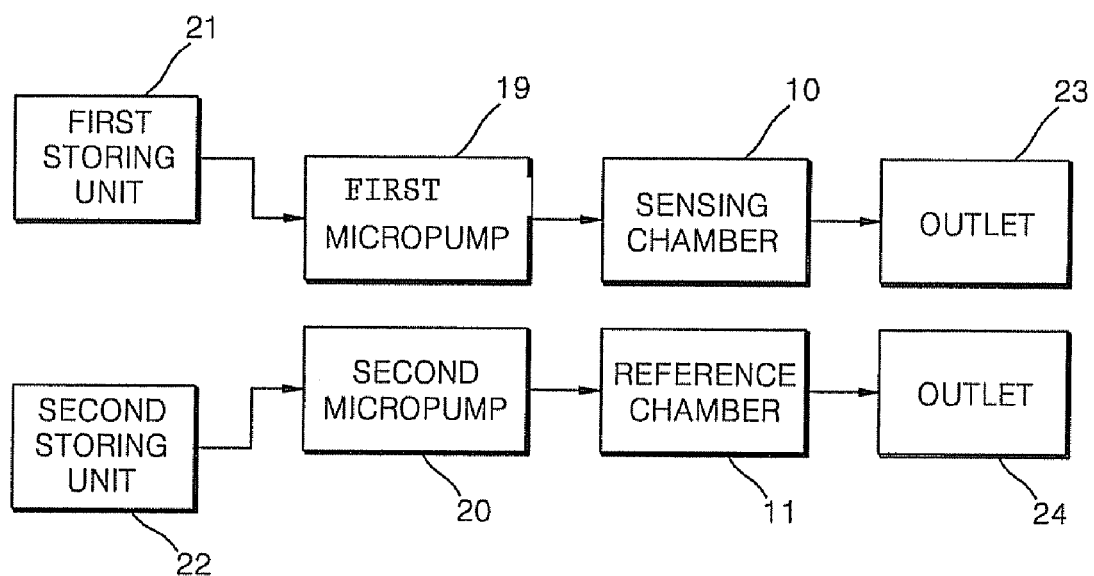
FIG. 2 illustrates an exemplary embodiment of an ionic material detecting device including the FET-based sensor according to the present invention.

FIG. 2 illustrates an exemplary embodiment of an ionic material detecting device including the FET-based sensor for detecting an ionic material according to the present invention.

Referring to FIG. 2, the ionic material detecting device including the FET is based sensor includes a sensing chamber 10 and a reference chamber 11. The sensing chamber 10 includes a reference electrode and a plurality of sensing FETs, and the reference chamber 11 includes a reference electrode and a plurality of reference FETs.

The ionic material detecting device may include a first storing unit 21, which stores a solution that will be supplied to the sensing chamber 10, and a first micropump 19, which supplies a solution from the first storing unit 21 to the sensing chamber 10.

In a similar way, the ionic material detecting device may include a second storing unit 22, which stores a solution that will be supplied to the reference chamber 11, and a second micropump 20, which supplies a solution from the second storing unit 22 to the reference chamber 11.

The ionic material detecting device may include an outlet 23 through which a solution flows out from the sensing chamber 10, and an outlet 24 through which a solution flows out from the reference chamber 11.

An exemplary embodiment provides a method of detecting an ionic material in which a low concentration of an ionic material can be detected with relatively high sensitivity.

A method of detecting an ionic material includes flowing a first solution into and out of a sensing chamber and a reference chamber of an FET-based sensor, flowing a second solution expected to contain an ionic material into and out of the sensing chamber while substantially continuously flowing the first solution into and out of the reference chamber, measuring the level of a current in a channel region between the source and drain of each of sensing and reference FETs while flowing the first and second solutions through the sensing chamber and the reference chamber, respectively, and correcting the current of the sensing FET by subtracting the current of the reference FET from the current of the sensing FET.

In an exemplary embodiment of a method of detecting an ionic material, the first solution, which is flowed into and out of the sensing chamber and the reference chamber, may be an electrolytic solution.

In an exemplary embodiment of a method of detecting an ionic material, the flowing of the first solution into and out of the sensing chamber and the reference chamber, and the flowing of the second solution through the sensing chamber, is performed under the same pressure. This is because the currents measured at the FETs may change due to changes in the applied pressure applied when flowing the first and/or second solution into the sensing and/or reference chambers, respectively.

In an exemplary embodiment of a method of detecting an ionic material, the current of the sensing FET can be corrected by subtracting the level of a current in one of the reference FETs from the level of a current in one of the sensing FETs. However, signals of a target biomolecule, such as drift signals spontaneously generated due to a reaction on the surface of the gate electrode and signals generated due to the pressure applied when flowing a solution into the chambers, cannot be generated.

Thus, the level of a current in the sensing FETs and the level of a current in the reference FETs may be the average of the levels of currents in sensing FETs and the average of the levels of currents in reference FETs. The level of a current in the sensing FETs and the level of a current in the reference FETs may be the average of the levels of currents of as many sensing FETs as possible and the average of the levels of currents of as many reference FETs as possible.

In an exemplary embodiment of an ionic material detecting method, the ionic material is not specifically limited. In one exemplary embodiment, the ionic material may be a biomolecule such as a protein or a nucleic acid.

The nucleic acid can be selected from the group consisting of DNA, RNA, PNA, LNA and a hybrid thereof. The protein can be selected from the group consisting of an enzyme, a substrate, an antigen, an antibody, a ligand, an aptamer, and a receptor.

In the following examples, results of detecting DNA using a conventional FET-based sensor for detecting an ionic material, which includes a single chamber, and a FET-based sensor for detecting an ionic material according to illustrated embodiments are shown.

Figure 3A:
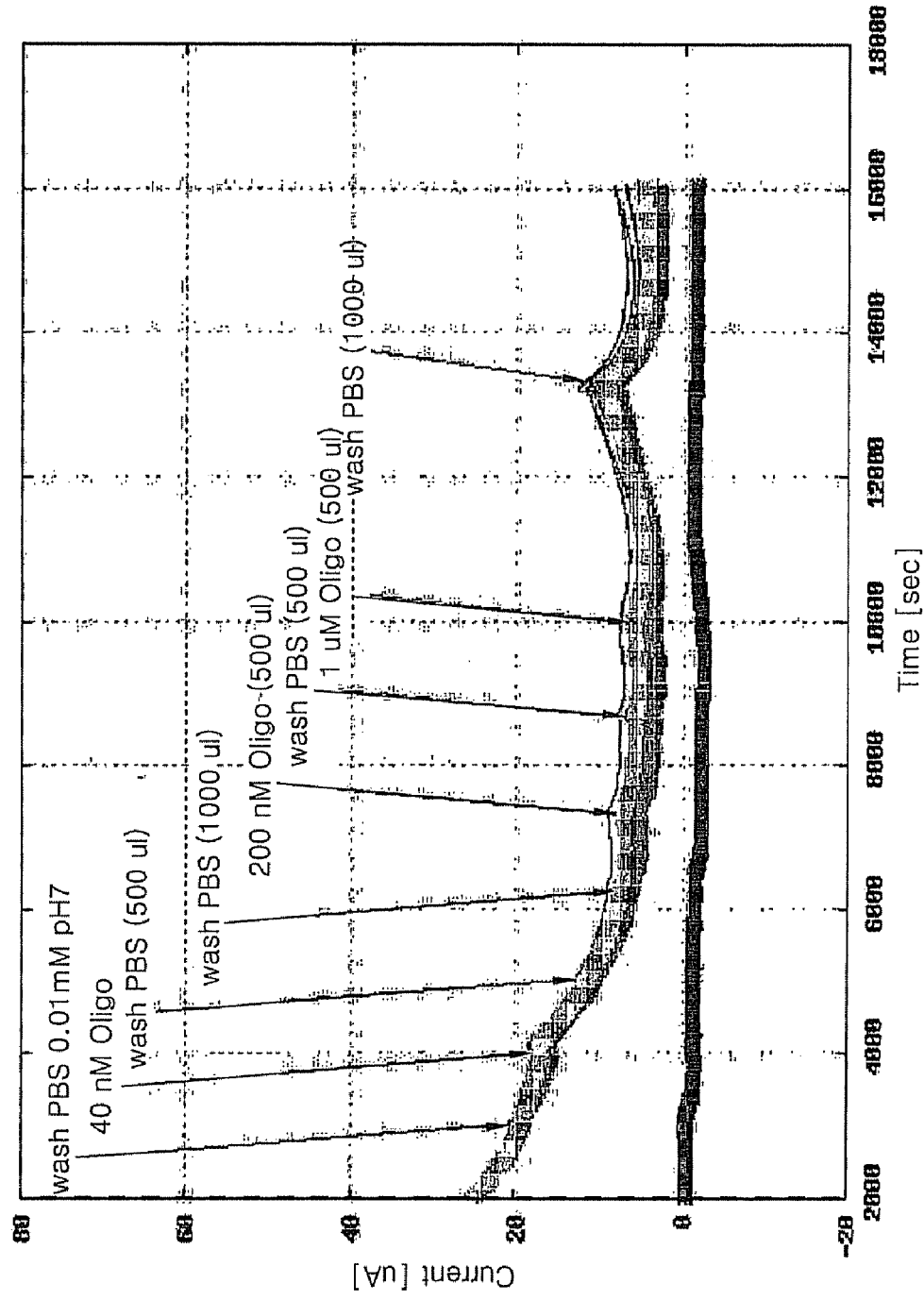
FIG. 3A is a graph illustrating the exemplary results of detecting DNA using a conventional FET-based sensor for ionic material detection including a single chamber of the prior art.
Figure 3B:
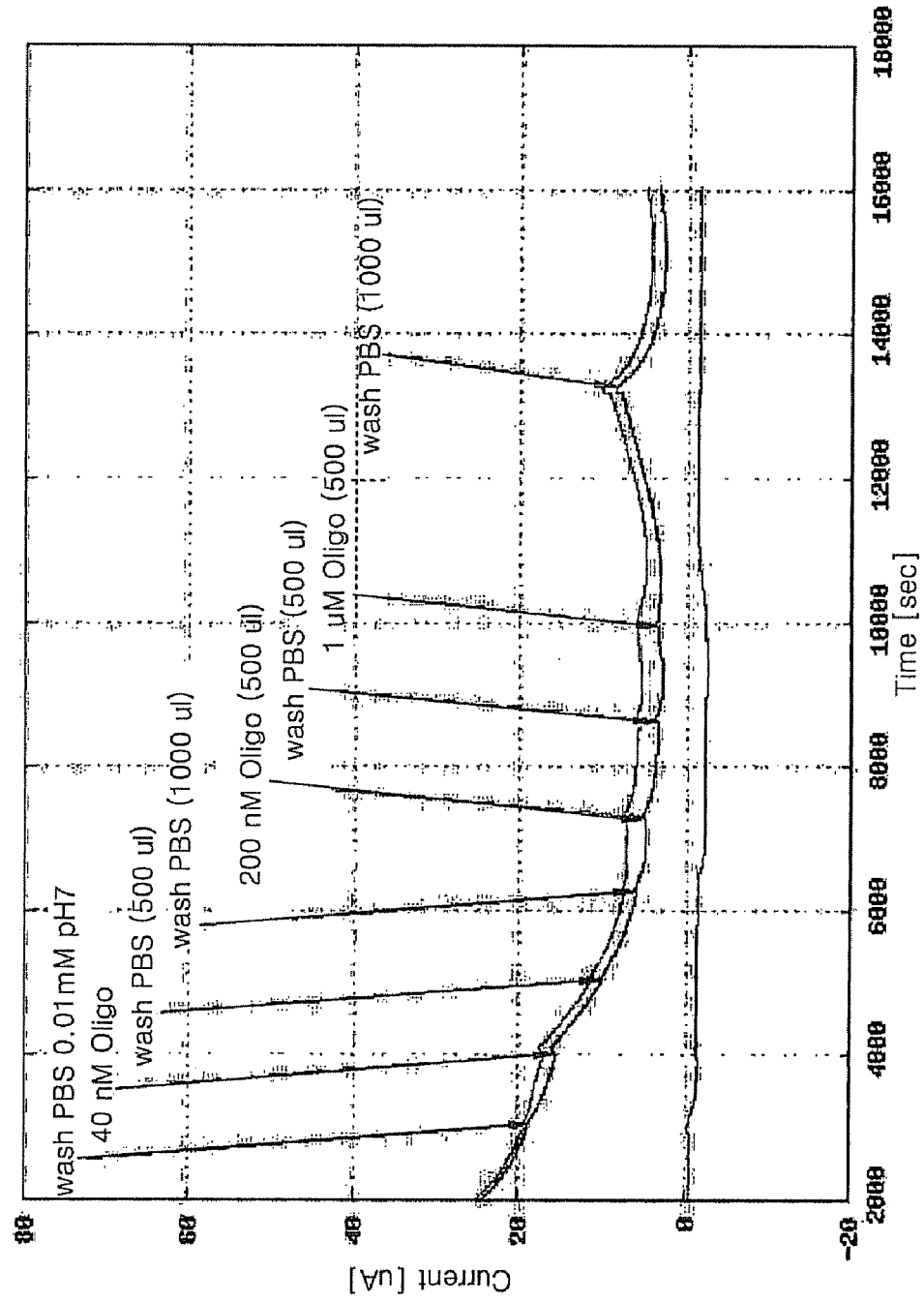
FIG. 3B is a graph illustrating the averages of the results in FIG. 3A.

When the conventional FET-based sensor including a signal chamber was used, DNA was not detected at all (refer to FIGS. 3A and 3B). On the other hand, when a FET-based sensor for detecting an ionic material according to illustrated embodiments was used, DNA was effectively detected (refer to FIGS. 4A through 5B).

The present invention will be described in detail with reference to exemplary embodiments. The invention, however, should not be construed as being limited to the embodiments set forth herein.

Hereinafter, the present invention will be described with reference to the following examples. These examples are for illustrative purposes only and are not intended to limit the scope of the invention.

Example 1

Manufacture of a FET-Based Sensor for Ionic Material Detection

A FET device was order-manufactured by X-FAB Semiconductor Foundries (Germany). The manufactured FET device included 192 FETs having the same structure and the same electrical characteristics in an array of 4×48. The FET device was manufactured using the equipment of X-FAB Semiconductor Foundries according to the company's own CMOS process. Although companies may have different standard CMOS processes, such differences are not a substantial factor affecting characteristics of the FET device. Therefore, the CMOS standard process of the company is not described herein.

A passivation layer and a gate electrode layer were removed from each of the FETs in an array to expose a polysilicon layer. Next, the exposed polysilicon layer on the surface of the FET was carefully washed with pure acetone and then with water and dried. The process of washing the substrate was performed using a wet station used in semiconductor manufacturing processes. The drying after the washing was performed using a spin drier.

Chamber sidewalls defining chambers were installed on the substrate with the array of FETs, and a platinum (Pt)-coated upper substrate functioning as a reference electrode was installed, thereby manufacturing a FET-based sensor for ionic material detection according to the illustrated embodiments including two chambers, e.g., a sensing chamber and a reference chamber.

Each of the sensing chamber and the reference chamber included 12 (i.e., 4×3) FET-based sensors each having an exposed gate surface area of 300 micrometers ($\mu$m)×100 $\mu$m. The remaining 24 FET-based sensors among a total of 48 (i.e., 4×12) FET-based sensors were covered by the chamber sidewalls in the manufacturing process and could not be included in the chambers.

Comparative Example 1

Manufacture of a FET Based Sensor for Ionic Material Detection Including a Single Chamber A passivation layer and a gate electrode layer were removed from each of 192 (i.e., 12×16) FETs in an array (X-FAB Semiconductor Foundries, Germany) described in Example 1 to expose a polysilicon layer.

Next, the surface of each FET with the exposed polysilicon layer was carefully washed in the same manner as in Example 1.

Chamber sidewalls for defining chambers were installed on the substrate with the array of FETs, and a platinum (Pt)-coated upper substrate functioning as a reference electrode was installed, thereby manufacturing a FET-based sensor for ionic material detection including a single chamber. The chamber included a total of 48 (i.e., 12×4) of FET-based sensors.

Experimental Example 1

DNA Detection Using a FET-Based Sensor for Ionic Material Detection Including a Single Chamber A 0.01 millimolar mM phosphate buffer solution ("PBS") (e.g., pH 7.0) and a solution containing 15-mer oligonucleotide (TGTTCTCTTGTCTTG) (SEQ. ID. NO. 1) were alternately flowed into and out of a chamber of the FET-based sensor manufactured in Experimental Example 1.

In particular, a 0.01 mM PBS solution, a 40 nanomolar (nM) oligonucleotide solution, 500 microliter ($\mu$l) of a 0.01 Mm PBS solution, 1000 $\mu$l of PBS, 500 $\mu$l of 200 nM oligonucleotide solution, 500 $\mu$l of PBS, and 500 $\mu$l of a 1 micromolar ($\mu$M) oligonucleotide solution, and 1000 $\mu$l of PBS were sequentially flowed into the chamber at 0.5 microliter per minute ($\mu$l/min) with an interval of several minutes to allow a previously injected solution to be completely flowed out of the chamber while a next solution was injected.

The level of a current in each of the 24 FETs, including 12 sensing FETs and 12 reference FETs, of the sensor manufactured in Comparative Example 1, was measured. The average of the levels of currents in the sensing FETs and the average of the levels of currents in the reference FETs were calculated. The level of the current in the sensing FET was corrected by subtracting the average level of the currents in the reference FETs from the average level of the currents in the sensing FETs. The results are shown in FIGS. 3A and 3B.

FIG. 3A is a graph illustrating the exemplary results of detecting DNA using a conventional FET-based sensor including a single chamber. FIG. 3B is a graph illustrating the averages of the results in FIG. 3A.

In FIG. 3A, two upper bold (e.g., shaded) lines denote the averages of the levels of currents in the sensing FETs and the reference FETs, respectively, and a lower bold line denotes corrected levels of currents in the sensing FETs obtained by subtracting the average level of currents of the reference FETs from the average level of currents of the sensing FETs. FIG. 3B is a graph of the averages of the levels of currents in the sensing FETs and the reference FETs, which correspond to the two upper bold lines in FIG. 3A.

FIGS. 3A and 3B show that DNA cannot be effectively detected using the levels of currents of the sensing FETs, even though the levels of currents of the sensing FETs are corrected based on the levels of currents of the reference FETs.

Experimental Example 2

DNA Detection Using a FET Based Sensor (First Experiment)

A 0.01 mM PBS buffer solution (pH 7.0) was flowed into and out of each of the sensing chamber and the reference chamber of the FET-based sensor manufactured in Example 1 under the same pressure through each chamber. Next, at a certain point of time, the PBS buffer solution was flowed into and out of the reference chamber while a solution containing 15-mer oligonucleotide (TGTTCTCTTGTCTTG) (SEQ. ID. NO. 1) was flowed into and out of the sensing chamber under the same pressure as the PBS buffer solution was flowed into and out of the reference chamber.

In particular, the PBS solution was injected three times into each of the sensing chamber and the reference chamber, and at a certain point of time, the PBS solution was flowed into the reference chamber while the 1 μM oilgonucleotide solution was flowed into the sensing chamber. Next, the PBS solution was flowed three times into each of the reference chamber and the sensing chamber. Lastly, air was pumped into the reference chamber and then the sensing chamber.

The levels of currents in 12 sensing FETs in the sensing chamber of the FET-based sensor manufactured in Example 1, and the levels of currents in 12 reference FETs in the reference chamber of the sensor were measured. The averages of the levels of currents of the sensing FETs and reference FETs were calculated. The levels of currents of the sensing FETs were corrected using a value obtained by subtracting the average level of currents of the reference FETs from the average level of currents of the sensing FETs. The results are shown in FIGS. 4A and 4B.

Figure 4A:
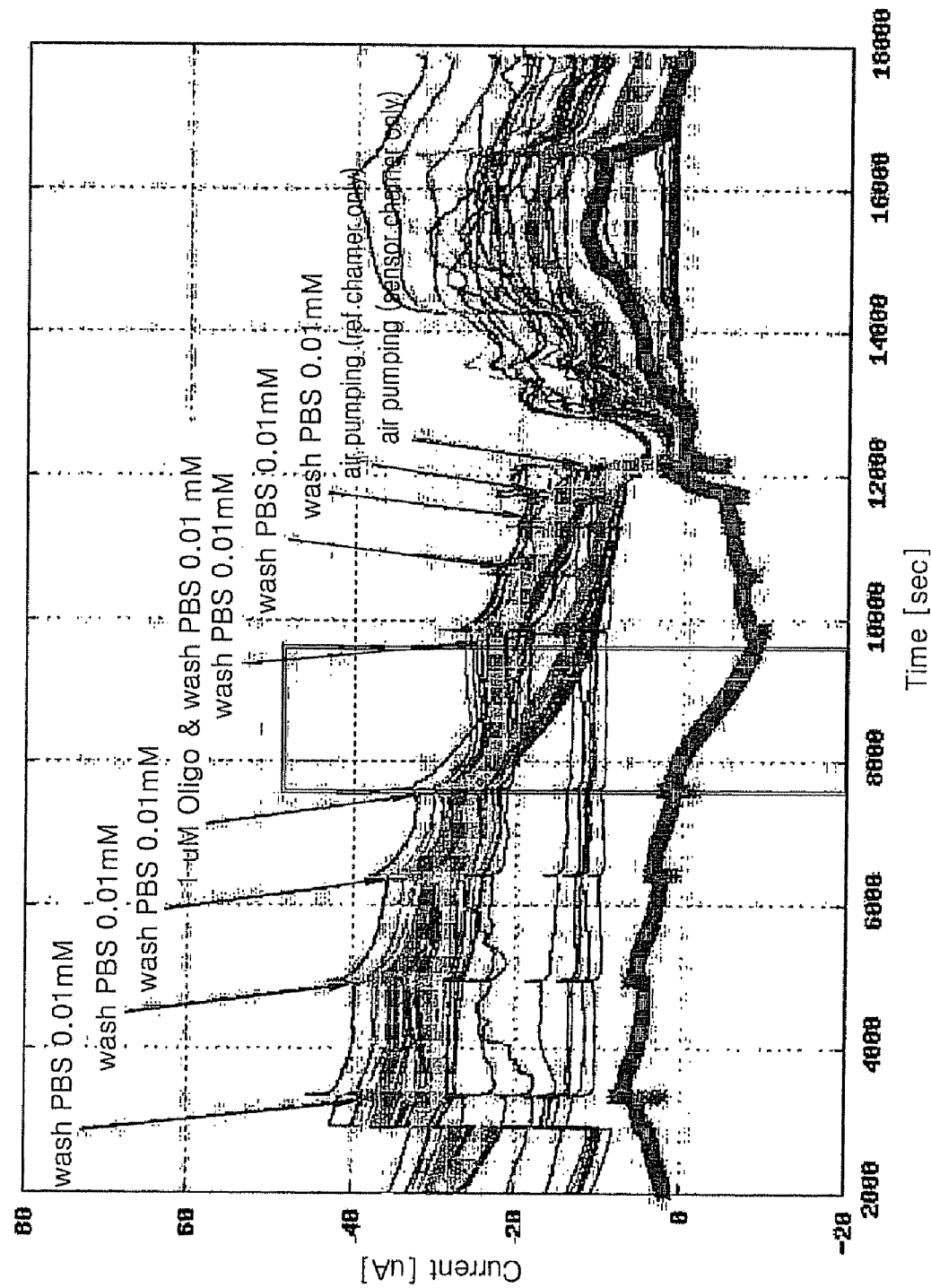
FIG. 4A is a graph illustrating the exemplary results of detecting DNA using an exemplary embodiment of a FET-based sensor for ionic material detection according to the present invention.

FIG. 4A is a graph illustrating the exemplary results of detecting DNA using a FET-based sensor for ionic material detection according to the present invention. FIG. 4B is a graph illustrating the averages of the results in FIG. 4A.

In FIG. 4A, two upper bold lines denote the averages of the levels of currents in the sensing FETs and the reference FETs, and a lower bold line denotes corrected levels of currents of the sensing FETs obtained by subtracting the average level of currents of the reference FETs from the average level of currents of the sensing FETs. Two upper bold lines refers to the lines starting from about 20 μA-30 μA. FIG. 4B is a graph of the averages of the levels of currents in the sensing FETs and the reference FETs, which correspond to the two upper bold lines in FIG. 4A.

Figure 4B:
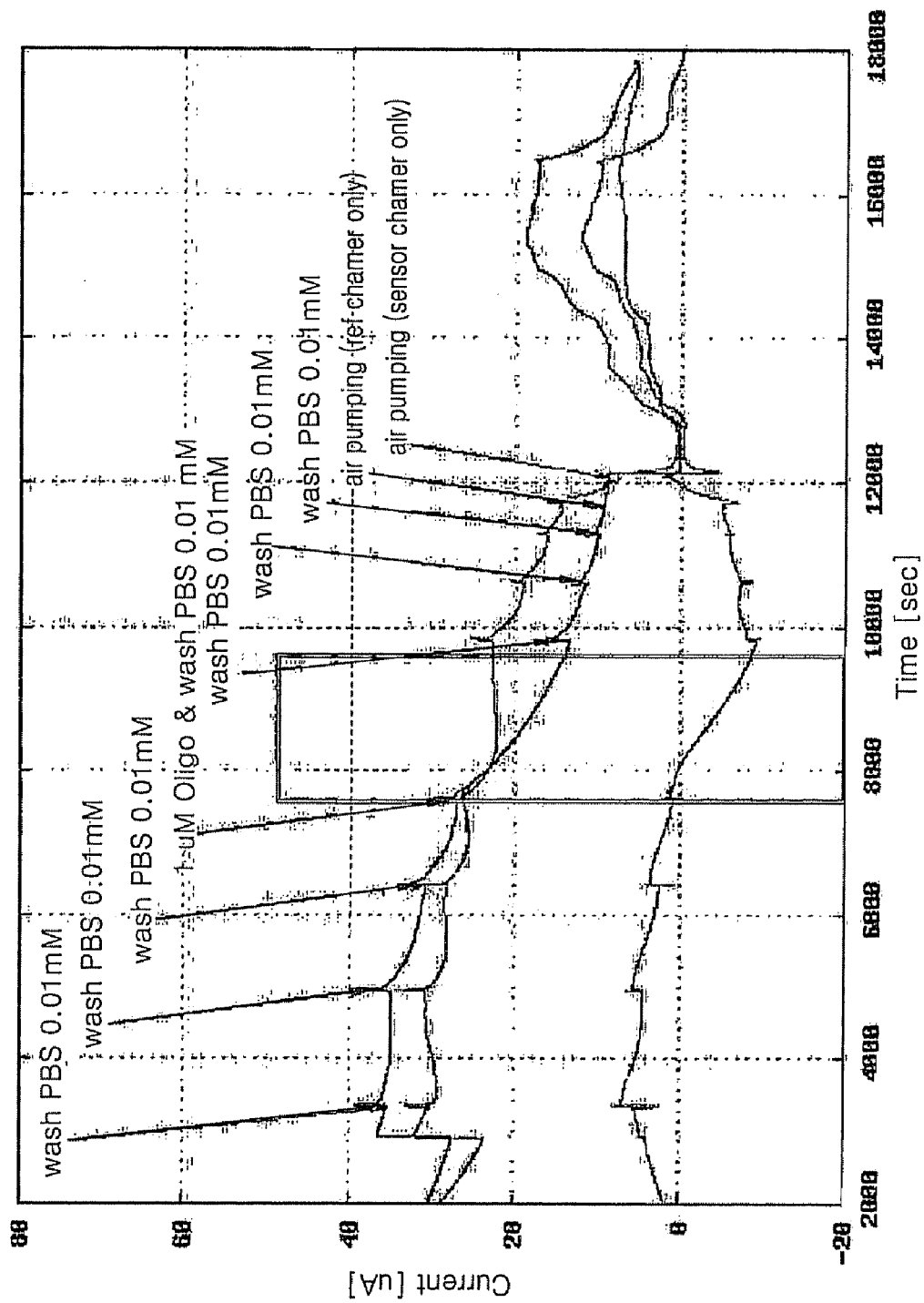
FIG. 4B is a graph illustrating the averages of the results in FIG. 4A.

As is apparent from FIGS. 4A and 4B, when using the FET-based sensor for ionic material detection of the illustrated embodiments, signals from a target biomolecule can be relatively clearly separated from noise, such as drift signals spontaneously generated due to a reaction on the surface of the gate electrode and signals generated due to the pressure applied when injecting a solution (refer to regions supported by rectangles in FIGS. 4A and 4B). Advantageously, the exemplary FET-based sensor for ionic material detection of the illustrated embodiments has a relatively high sensitivity, and thus can be used to detect a low-concentration ionic material, even a biomolecule, such as a nucleic acid or protein.

Experimental Example 3

DNA Detection Using a FET-Based Sensor (Second Experiment)

DNA detection was performed using the FET-based sensor of the illustrated embodiments manufactured in Example 1 in the same manner as in Example 1, except that the timing of injecting the solutions was slightly varied. The results are shown in FIGS. 5A and 5B.

Figure 5A:
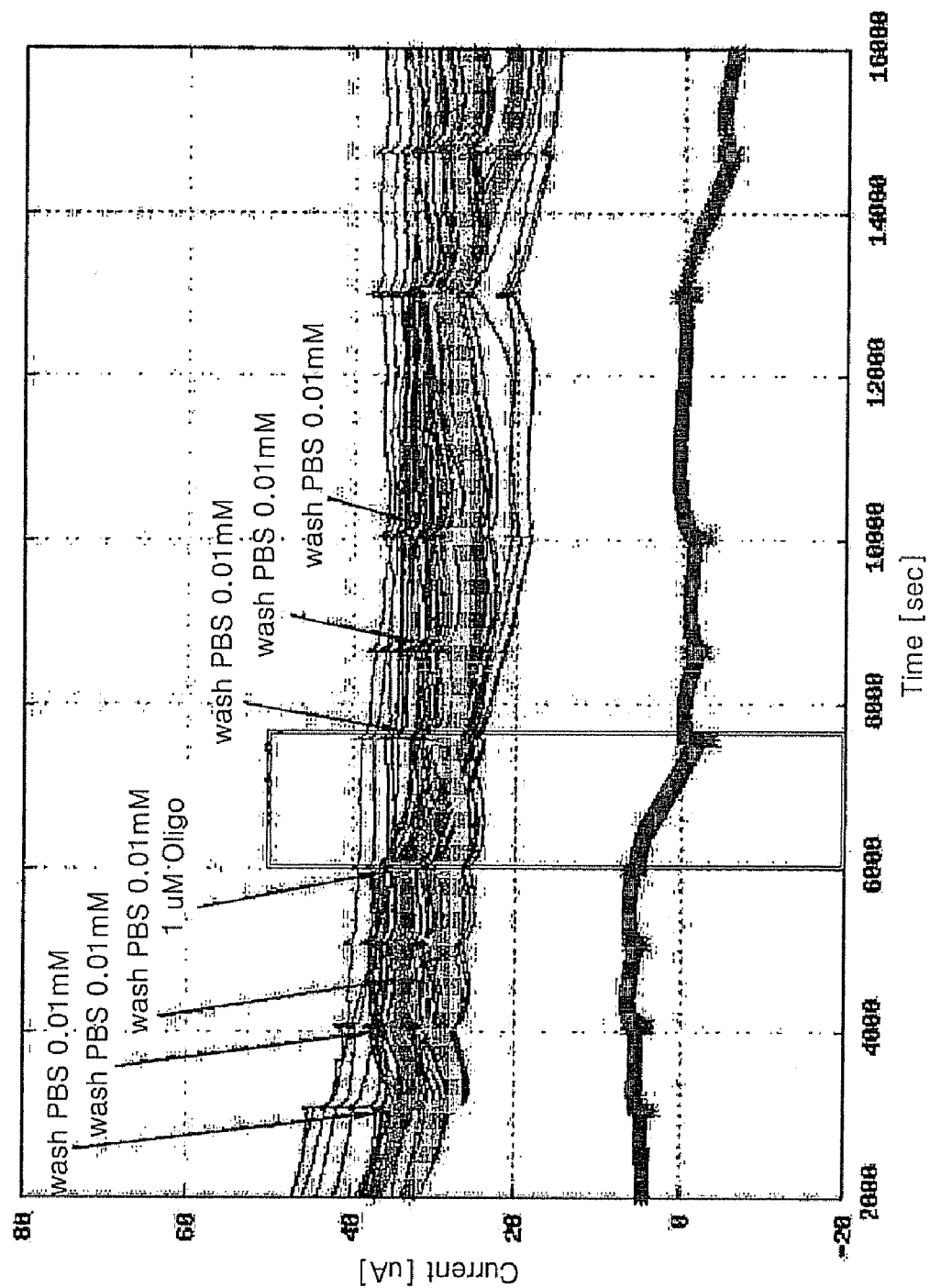
FIG. 5A is a graph illustrating the exemplary results of detecting DNA using another exemplary embodiment of a FET-based sensor for ionic material detection according to the present invention.

FIG. 5A is a graph illustrating the exemplary results of detecting DNA using a FET-based sensor for ionic material detection according to the present invention. FIG. 5B is a graph illustrating the averages of the results in FIG. 5A.

In FIG. 5A, two upper bold lines denote the averages of the levels of currents in the sensing FETs and the reference FETs, and a lower bold line denotes corrected levels of currents in the sensing FETs obtained by subtracting the average level of currents of the reference FETs from the average level of currents of the sensing FETs. FIG. 5B is a graph of the averages of the levels of currents in the sensing FETs and the reference FETs, which correspond to the two upper bold lines in FIG. 5A.

As is apparent from FIGS. 5A and 5B, when using the FET-based sensor for ionic material detection of the illustrated embodiments, signals from a target biomolecule can be relatively clearly separated from noise, such as drift signals spontaneously generated due to a reaction on the surface of the gate electrode and signals generated due to the pressure applied when injecting a solution (refer to regions supported by rectangles in FIGS. 5A and 5B). Thus, the FET-based sensor for ionic material detection of the illustrated embodiments has a relatively high sensitivity, and thus can be used to detect a low-concentration ionic material, even a biomolecule, such as a nucleic acid or protein.

As described above in the illustrated exemplary embodiments, signals from a target biomolecule can be relatively clearly separated from noise, such as drift signals spontaneously generated due to a reaction on the surface of the gate electrode and signals generated due to the pressure applied when injecting a solution. A FET-based sensor for ionic material detection of the illustrated embodiments has a relatively high sensitivity, and thus can be used to detect a low-concentration ionic material, even a biomolecule, such as a nucleic acid or protein, with improved robustness to noise.

While this invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A FET (field-effect transistor)-based sensor for detecting an ionic material, the sensor comprising:
a sensing chamber including a reference electrode and a plurality of sensing FETs, wherein the sensing chamber is defined by a lower substrate including the plurality of sensing FETs, sidewalls, and an upper substrate functioning as the reference electrode; and
a reference chamber including a reference electrode and a plurality of reference FETs, wherein the reference chamber is defined by the lower substrate including the plurality of reference FETs, sidewalls, and the upper substrate function as the reference electrode.

2. The FET-based sensor of claim 1, wherein the sensing FETs and the reference FETs have a same structure and a same electrical characteristics.

3. The FET-based sensor of claim 1, wherein the sensing FETs and the reference FETs are each arranged in an array form.

4. The FET-based sensor of claim 1, wherein each of the sensing and reference FETs comprises:
a substrate;
a source and a drain formed in side regions of the substrate and doped with a polarity opposite to the substrate; and
a gate formed on the substrate connecting the source and the drain.

5. The FET-based sensor of claim 4, wherein the gate comprises an oxide layer and a polysilicon layer on the oxidation layer.

6. The FET-based sensor of claim 1, wherein the ionic material is a biomolecule.

7. The FET-based sensor of claim 6, wherein the biomolecule is a nucleic acid or a protein.

8. The FET-based sensor of claim 7, wherein the nucleic acid is selected from the group consisting of DNA, RNA, PNA, LNA and a hybrid thereof.

9. The FET-based sensor of claim 7, wherein the protein is selected from the group consisting of an enzyme, a substrate, an antigen, an antibody, a ligand, an aptamer and a receptor.

10. The FET-based sensor of claim 1, wherein each of the sensing chamber and the reference chamber further comprises an inlet through which a solution flows into the chamber and an outlet through which a solution flows out of the chamber.

11. The FET-based sensor of claim 1, wherein each of the sensing chamber and the reference chamber is connected to a micropump pumping a solution into and out of the chambers.

12. An ionic material detecting device comprising the FET-based sensor of claim 1.

* * * * *